(12) United States Patent
Kim et al.

(10) Patent No.: US 8,332,997 B2
(45) Date of Patent: Dec. 18, 2012

(54) DENTAL PROSTHESIS MANUFACTURING MACHINE

(75) Inventors: Jae Doc Kim, Yongin-Si (KR); Yeong Kyun Kim, Yougin-Si (KR); Sung Kuk Kim, Yongin-Si (KR); Heon Joo Kim, Yongin-Si (KR); Jae Yun Park, Yongin-Si (KR)

(73) Assignee: Vatech Co., Ltd, Yongin-si (KR)

( * ) Notice: Subject to any disclaimer, the term of this patent is extended or adjusted under 35 U.S.C. 154(b) by 791 days.

(21) Appl. No.: 12/449,651

(22) PCT Filed: Jul. 31, 2008

(86) PCT No.: PCT/KR2008/004457
§ 371 (c)(1),
(2), (4) Date: Aug. 19, 2009

(87) PCT Pub. No.: WO2010/002057
PCT Pub. Date: Jan. 7, 2010

(65) Prior Publication Data
US 2011/0239464 A1   Oct. 6, 2011

(30) Foreign Application Priority Data

Jul. 1, 2008 (KR) .................. 10-2008-0063635

(51) Int. Cl.
| | |
|---|---|
| *B23P 23/00* | (2006.01) |
| *B23C 3/00* | (2006.01) |
| *B23C 1/04* | (2006.01) |
| *B23C 1/14* | (2006.01) |

(52) U.S. Cl. ............ 29/27 R; 29/36; 29/28; 29/40; 82/129; 82/121; 451/362; 451/246; 409/167; 409/192

(58) Field of Classification Search ........... 29/36, 40, 29/39, 50, 33 J, 27 C, 27 R, 28; 82/120, 82/121, 159, 129; 409/192, 203, 213, 217, 409/165, 166, 167; 451/362, 246
See application file for complete search history.

(56) References Cited

U.S. PATENT DOCUMENTS

| | | | |
|---|---|---|---|
| 4,730,373 A * | 3/1988 | Senoh | ............ 29/26 A |
| 5,266,030 A | 11/1993 | Van Der Zel | |
| 5,916,498 A | 6/1999 | Hofmann et al. | |
| 6,394,880 B1 * | 5/2002 | Basler et al. | ............ 451/28 |
| 6,766,217 B1 | 7/2004 | Hamada | |

(Continued)

FOREIGN PATENT DOCUMENTS

DE   4030175 A1 *  3/1992
(Continued)

OTHER PUBLICATIONS

Machine Translation of DE 4030175, which DE '175 was published Mar. 1992.*

*Primary Examiner* — Erica E Cadugan
(74) *Attorney, Agent, or Firm* — Stein McEwen, LLP

(57) ABSTRACT

A dental prosthesis manufacturing machine is disclosed. The machine includes two spindles each having a roughing tool and a finishing tool, a workpiece holder for holding a workpiece which forms the dental prosthesis, and a base supporting the two spindles and the workpiece holder. The machine is capable of simply alternating the roughing tool with the finishing tool according to the accuracy required when the workpiece is machined.

5 Claims, 2 Drawing Sheets

U.S. PATENT DOCUMENTS

| | | | |
|---|---|---|---|
| 6,920,679 B2 * | 7/2005 | Hessbruggen et al. | 29/27 C |
| 6,953,383 B2 * | 10/2005 | Rothenberger | 451/11 |
| 7,156,637 B1 | 1/2007 | Kutsch et al. | |
| 2006/0269373 A1 * | 11/2006 | Duncan et al. | 409/64 |
| 2007/0197361 A1 * | 8/2007 | Boehler et al. | 483/31 |
| 2011/0179630 A1 * | 7/2011 | Kim et al. | 29/592 |

FOREIGN PATENT DOCUMENTS

| | | |
|---|---|---|
| JP | 2002-273655 A | 9/2002 |
| JP | 2008-509745 T | 4/2008 |
| KR | 10-2001-0026892 A | 4/2001 |
| KR | 10-0760073 B1 | 9/2007 |

* cited by examiner

DENTAL PROSTHESIS MANUFACTURING MACHINE

This is a National Phase Application filed under 35 U.S.C. 371 as a national stage of PCT/KR2008/004457, with the filing date of Jul. 31, 2008, an application claiming priority benefit from Korean Patent Application No. 10-2008-0063635, filed Jul. 1, 2008, the entire content of each of which is hereby incorporated by reference in its entirety.

TECHNICAL FIELD

The present invention relates, in general, to a dental prosthesis manufacturing machine and, more particularly, to a dental prosthesis manufacturing machine which is capable of simply alternating a roughing tool with a finishing tool according to the accuracy required when a workpiece is machined.

BACKGROUND ART

When a tooth must be extracted due to external injury or dental caries, a dental prosthesis is used to form the natural inter-dental papilla or gingiva and recover mastication, pronunciation and aesthetic functions. The dental prosthesis is referred to as an artificial tooth or a false tooth. Further, the dental prosthesis means an artificial substitute for a missing natural tooth or tissue associated therewith. Such a dental prosthesis has been essentially used to prevent a tooth adjacent to an extracted tooth from moving to an abnormal location during dental treatment period.

Meanwhile, all dental prostheses have been manufactured through the manual operation of a dental technician. However, recently, technology dealing with a prosthesis manufacturing machine which is capable of more efficiently and precisely manufacturing a dental prosthesis has been developed.

For example, Japanese Patent Laid-Open Publication No. 2002-0273655 disclosed a dental prosthesis manufacturing machine using a structure for measuring the accurate positional data of first and second machining tools which machine the workpiece of the dental prosthesis. Further, Japanese Patent Laid-Open Publication No. 2008-0509745 disclosed a dental prosthesis manufacturing machine using a structure which axially offsets first and second spindles from each other so as to improve the accuracy of prosthesis manufacturing work.

The conventional machines are advantageous in that they improve the manufacturing accuracy of a dental prosthesis. However, when a portion requiring a high degree of accuracy in the manufacturing process of a dental prosthesis is machined using the conventional machines, existing machining tools are disconnected from the spindles, and thereafter precision machining tools are attached to the spindles to perform precision machining work. Alternatively, the workpiece is transferred to another dental prosthesis manufacturing machine which conducts more precise machining work. Thus, the conventional machines are problematic in that it is complicated to manufacture a dental prosthesis. Such a process is disadvantageous in terms of time and cost.

DISCLOSURE

Technical Problem

Accordingly, an object of the present invention is to provide a dental prosthesis manufacturing machine, which overcomes the above problems occurring in the prior art and solves technical problems lying therein.

Another object of the present invention is to provide a dental prosthesis manufacturing machine, which is capable of machining a workpiece by simply alternating two tools having different machining accuracy with each other, according to the accuracy required when the workpiece is machined.

Technical Solution

In order to accomplish the above objects, the present invention provides a dental prosthesis manufacturing machine, including first and second spindles each having a roughing tool and a finishing tool which rotate around corresponding rotating axes, a workpiece holder for holding a workpiece which forms the dental prosthesis, and a base supporting the first and second spindles and the workpiece holder, wherein the first and second spindles are placed on the same axis (first axis) in such a way as to face each other, the workpiece holder moves on a second axis intersecting the first axis and a third axis perpendicular to the first and second axes such that the workpiece held by the workpiece holder is placed between the first and second spindles, and the workpiece is machined by alternately using the roughing tool and the finishing tool according to accuracy which is required when the workpiece held by the workpiece holder is machined.

That is, the first spindle and the second spindle may move on the first axis, and the workpiece holder may move on the second axis and the third axis, thus machining the workpiece three-dimensionally. Each spindle may be provided with the roughing tool and the finishing tool, so that the roughing tool alternates with the finishing tool when precision machining work is required.

According to an aspect of this invention, the first and second spindles move on the first axis, and the workpiece holder moves on the second axis and the third axis which is perpendicular to the first and second axes while rotating around the second axis.

The rotating structure of the workpiece holder permits the easy machining of a portion which is difficult to be machined when the workpiece is machined by the movement of the spindles and the workpiece holder relative to the first, second and third axes.

The alternation of the roughing tool and the finishing tool may be performed through various constructions. Either of the roughing tool and the finishing tool may be located at a position at which the workpiece can be machined, and the roughing tool may alternates with the finishing tool by rotating each of the spindles 180 degrees.

Further, the roughing tool may alternate with the finishing tool by moving the workpiece holder on the second axis such that the workpiece is displaced from a position between the roughing tools or the finishing tools to a position between the finishing tools or the roughing tools.

The two roughing tools may be provided on the first and second spindles in such a way that they face each other and rotating axes thereof are not aligned with each other, and the two finishing tools may be provided on the first and second spindles in such a way that they face each other and rotating axes thereof are not aligned with each other. That is, if the rotating axes are aligned with each other, pressure acting on the workpiece is large, so that the workpiece may be undesirably broken or damaged. Especially when a thin part is machined, the possibility of damage increases. For the reasons, the rotating axes of the roughing tools or finishing tools are configured such that they are not aligned with each other, thus preventing the damage to the workpiece.

Advantageous Effects

According to the present invention, a dental prosthesis manufacturing machine is capable of machining a workpiece by simply alternating two tools having different machining accuracy with each other, according to the accuracy required when the workpiece is machined, thus reducing time and cost required for the manufacture of a dental prosthesis.

BEST MODE

Hereinafter, the preferred embodiments of the present invention will be described with reference to the accompanying drawings. However, since the embodiments aid in understanding the present invention, the scope of the present invention is not limited to the embodiments.

Figure 1:
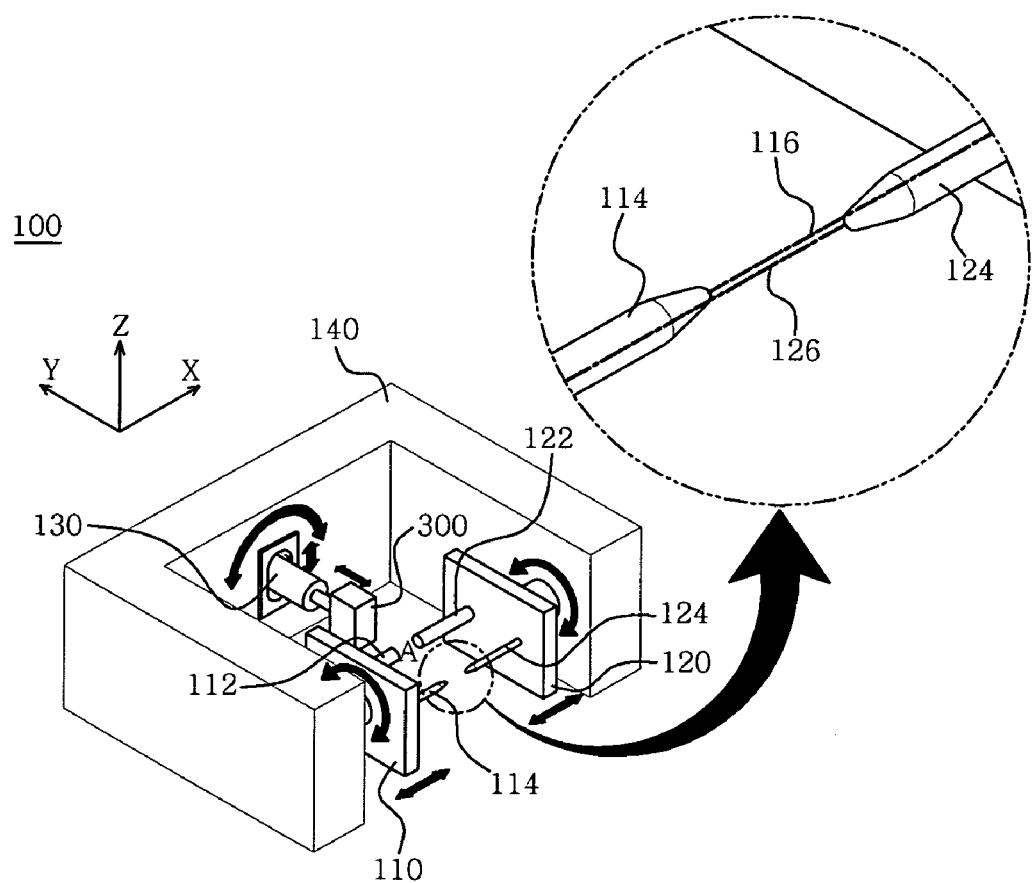
FIG. 1 is a schematic view illustrating a dental prosthesis manufacturing machine according to an embodiment of the present invention.

FIG. 1 is a schematic view illustrating a dental prosthesis manufacturing machine according to an embodiment of the present invention.

Referring to FIG. 1, the dental prosthesis manufacturing machine 100 includes a first turret or spindle 110 equipped with a roughing tool 112 and a finishing tool 114, a second turret or spindle 120 equipped with a roughing tool 122 and a finishing tool 124, a workpiece holder 130 for holding a workpiece 300, and a base 140.

Each of the roughing tools 112 and 122 and the finishing tools 114 and 124 rotates around its rotating axis to machine the workpiece 300. A drive motor is installed in each of the first and second spindles 110 and 120 to supply power for rotating the roughing tools 112 and 122 and the finishing tools 114 and 124.

In order to machine the workpiece three-dimensionally, the first spindle 110 and the second spindle 120 move on a first axis (X-axis), and the workpiece holder 130 moves on a second axis (Y-axis) and a third axis (Z-axis) while rotating around the second axis (Y-axis).

When the workpiece 300 is machined to manufacture the dental prosthesis, first, the workpiece 300 is located at a portion A and machined using the roughing tools 112 and 122. Afterwards, each of the first and second spindles 110 and 120 rotates 180 degrees, so that the finishing tools 114 and 124 are located at the portion A. Thereby, work which requires a high degree of accuracy and is difficult to be performed with the roughing tools 112 and 122 is conducted using the finishing tools 114 and 124.

The two finishing tools 114 and 124 which are coupled to the first and second spindles 110 and 120, respectively, in such a way as to face each other are configured so that the rotating axes 116 and 126 of the finishing tools 114 and 124 are not aligned with each other. The enlarged portion of FIG. 1 shows only the finishing tools 114 and 124. The configuration wherein rotating axes are not aligned with each other is identically applied to the two roughing tools 112 and 122.

MODE FOR INVENTION

Figure 2:
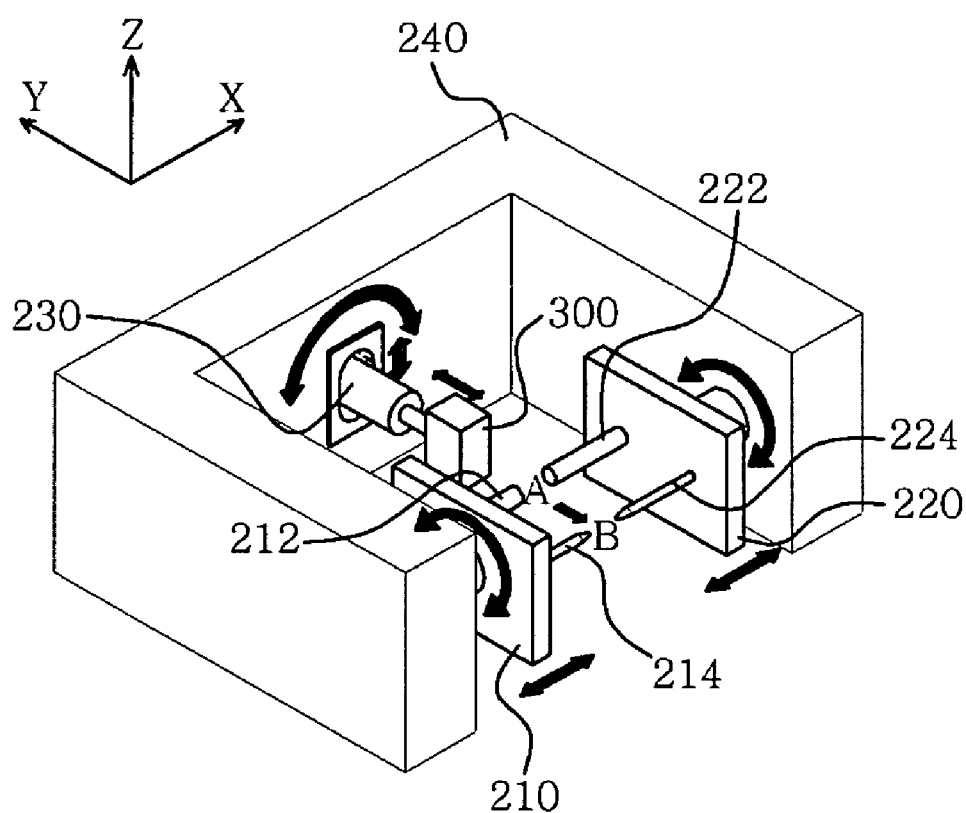
FIG. 2 is a schematic view illustrating a dental prosthesis manufacturing machine according to another embodiment of the present invention.

FIG. 2 is a schematic view illustrating a dental prosthesis manufacturing machine according to another embodiment of the present invention.

Referring to FIG. 2, first, a workpiece 300 is located at a portion A, so that the workpiece is machined using roughing tools 212 and 222. Next, a workpiece holder 230 extends along a second axis (Y-axis), so that the workpiece of the workpiece holder is located at a portion B where the machining operation using finishing tools 214 and 224 is carried out. Thereby, machining operation which requires a high degree of accuracy and is thus difficult to be performed using the roughing tools 212 and 222 is conducted using the finishing tools 214 and 224.

The duplicate description will be omitted herein because the dental prosthesis manufacturing machine of FIG. 2 has the same operational construction as that of FIG. 1 except for the construction which changes a roughing operation into a finishing operation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, the present invention provides a dental prosthesis manufacturing machine, which is capable of machining a workpiece by simply alternating two tools having different machining accuracy with each other, according to the accuracy required when the workpiece is machined. The dental prosthesis manufacturing machine according to the present invention is applicable in the dental field, and allows the dental prosthesis to be more efficiently and accurately manufactured.

The invention claimed is:

1. A dental prosthesis manufacturing machine, comprising:
   first and second indexable turrets configured to be indexed about a common first axis, each turret having a roughing tool and a finishing tool, which tools are each configured to be driven to rotate around a respective corresponding rotating axis to machine a workpiece to form the dental prosthesis;
   a workpiece holder for holding the workpiece which forms the dental prosthesis; and
   a base supporting the first and second turrets and the workpiece holder, wherein
   the first and second turrets are placed on the first axis in such a way as to face each other, the workpiece holder moves along and rotates about a second axis intersecting the first axis, and the workpiece holder moves along a third axis perpendicular to the first and second axes such that the workpiece held by the workpiece holder is placed between the first and second turrets, the rotating axes of the tools each intersecting a plane formed by the second and third axes, and the workpiece is machined by alternately using the roughing tools and the finishing tools according to accuracy which is required when the workpiece held by the workpiece holder is machined.

2. The dental prosthesis manufacturing machine according to claim 1, wherein the first and second turrets move along the first axis.

3. The dental prosthesis manufacturing machine according to claim 1, wherein the roughing tools alternate with the finishing tools such that either of the roughing tools and the finishing tools are located at a position at which the workpiece can be machined, and the roughing tools alternate with the finishing tools by rotating each of the turrets 180 degrees about the first axis, thus machining the workpiece.

4. The dental prosthesis manufacturing machine according to claim 1, wherein the roughing tools alternate with the finishing tools by moving the workpiece holder along the second axis such that the workpiece is displaced from a position between the roughing tools or the finishing tools to a position between the finishing tools or the roughing tools, respectively.

5. The dental prosthesis manufacturing machine according to claim 1, wherein the two roughing tools are provided on the first and second turrets in such a way that they face each other and the rotating axes thereof are not aligned with each other, and the two finishing tools are provided on the first and second turrets in such a way that they face each other and the rotating axes thereof are not aligned with each other.

* * * * *